United States Patent
Majeed et al.

(10) Patent No.: US 6,960,300 B2
(45) Date of Patent: Nov. 1, 2005

(54) PROCESS FOR PREPARING WATER SOLUBLE DITERPENES AND THEIR APPLICATIONS

(75) Inventors: Muhammed Majeed, Piscataway, NJ (US); Arvind Kumar, Edison, NJ (US); Kalyanam Nagabhushanam, North Brunswick, NJ (US); Subbalakshmi Prakash, Piscataway, NJ (US)

(73) Assignee: Sami Labs Limited, Bangalore (IN)

( * ) Notice: Subject to any disclaimer, the term of this patent is extended or adjusted under 35 U.S.C. 154(b) by 31 days.

(21) Appl. No.: 10/605,086

(22) Filed: Sep. 8, 2003

(65) Prior Publication Data

US 2005/0051483 A1 Mar. 10, 2005

(51) Int. Cl.$^7$ .......................... B01D 11/02; B01D 37/00; A61K 9/08
(52) U.S. Cl. .......................... 210/634; 23/299; 210/767; 424/400; 424/484; 424/725; 514/455; 514/909; 514/913; 516/204
(58) Field of Search ................................. 210/634, 639, 210/806, 767; 424/484, 486, 725, 400; 514/58, 445, 455, 772.2, 909–913; 549/389; 23/299; 516/204

(56) References Cited

U.S. PATENT DOCUMENTS

| | | | | |
|---|---|---|---|---|
| 4,476,140 A | * | 10/1984 | Sears et al. | 514/455 |
| 5,070,209 A | * | 12/1991 | Shutske | 549/228 |
| 5,302,730 A | * | 4/1994 | Tatee et al. | 549/389 |
| 5,804,596 A | * | 9/1998 | Majeed et al. | 514/455 |
| 5,846,992 A | * | 12/1998 | Conway et al. | 514/392 |
| 6,346,273 B1 | * | 2/2002 | Saettone et al. | 424/486 |
| 6,407,079 B1 | * | 6/2002 | Muller et al. | 514/58 |
| 6,471,972 B1 | * | 10/2002 | Bonte et al. | 424/401 |
| 6,540,895 B1 | * | 4/2003 | Spence et al. | 204/450 |

* cited by examiner

*Primary Examiner*—Joseph Drodge
(74) *Attorney, Agent, or Firm*—Arent Fox PLLC

(57) ABSTRACT

Aqueous solutions of diterpenes such as Forskolin, its congeners, analogs and derivatives, up to approximately 6% concentration, are prepared using suitably substituted cyclodextrin as a solubilizing agents. In the absence of cyclodextrin, some diterpenes such as Forskolin are soluble in water only to concentrations of about 0.001%. Such aqueous solutions find applications in topical and systemic use, as pharmaceutical, cosmeceutical, nutraceutical preparations containing diterpenes such as Forskolin and congeners.

7 Claims, No Drawings

PROCESS FOR PREPARING WATER SOLUBLE DITERPENES AND THEIR APPLICATIONS

BACKGROUND OF INVENTION

1. Field of Invention

The invention describes methods to prepare clear solutions of diterpenes, such as Forskolin and its congeners that are sparingly soluble or insoluble in water, of concentrations 0.09% to 6%, for convenient use in ophthalmic preparations as well as in topical, oral, injectable and other dosage forms, for human and veterinary use.

2. Description of Prior Art

Certain active pharmaceutical ingredients are inherently insoluble or very sparingly soluble in water or in aqueous vehicles. Very often their intended use may require their application in water or in aqueous vehicles. To achieve therapeutically active concentrations of such water insoluble active pharmaceutical ingredients in stable form has always been actively pursued. While the technique of molecular structural manipulation of the active pharmaceutical ingredient that is insoluble in water could be adopted, incorporating structural features that promote aqueous solubility may result in the attenuation or modification of the intended desired pharmacological properties. Hence it maybe most desirable to invent methods of solubilizing the active ingredients in their native structural form by other means.

Aqueous solubility of drugs is a desirable feature from many angles. Aqueous formulations are sterilizable by standard techniques such as filtration etc to render such preparations suitable for systemic administration. Also aqueous preparations are preferable in dermatological, gynecological, otological, rhinological and on mucous membrane applications. Especially useful are aqueous ophthalmic preparations of drugs.

Forskolin (CAS no 66575-29-9) is a naturally occurring labdane diterpene from Coleus forskohlii (Bhat, S. V.; Bajwa, B. S.; Dornauer, H.; de Souza, N. J.; Fehlabar, H.-W.; Tetrahedron Lett., (1977), 18, 1669). It has several desirable pharmacological properties.

Forskolin displays positive inotropic, antihypertensive and broncho-spasmolytic activity; (Bhat, S. V.; Dohadwalla, A. N.; Bajwa, B. S.; Dadkar, N.; Dornauer, H.; de Souza, N. J.; J Med Chem., (1983), 26, 486).

It lowers intraocular pressure (Caprioli J, Sears M.; Lancet (1983); April 30;1(8331):958–60;. Badian M et al.; Klin Monatsbl Augenheilkd (1984);185:5226, Zeng S, et al. Yan Ke Xue Bao (1995);11:173–176, Lee P Y, et al.; Arch Ophthalmol (1987);105:249–252,. Meyer B H, et al. S Afr Med J. (1987);71:570–571; Seto C, et al.; Jpn J Ophthalmol (1986);30:238–244.; Burstein N I et al. Exp Eye Res (1984) ;39:745–749; Brubaker R F et al. Arch Ophthalmol (1987); 105:637–641).

Diverse biological activities are observed by raising the levels of cAMP, and as a result activating protein kinase. Such properties have led to numerous uses of Forskolin. Due to such activities, more than 1500 citations dealing with the physiological properties of Forskolin appeared in Chemical Abstracts in 2001. However, Forskolin is highly insoluble in water.

Intensive efforts have been made on the molecular manipulation of Forskolin to make such derivatives of Forskolin as will be water soluble. Such attempts have always met with mixed success (Lal, B.; Gangopadhyay, A. K.; Rajagopalan, R.; Ghate, A. V.; Bioorganic & Medicinal Chemistry, (1998), 6(11), 2061–2073; Lal, B.; Gangopadhyay, A. K.; Gidwani, R. M.; Fernandez, M.; Rajagopalan, R.; Ghate, A. V.; Bioorganic & Medicinal Chemistry, (1998), 6(11), 2075–2083).

As an alternative to chemical manipulations of the drug molecular structure, physicochemical techniques of enhancing the solubility of the underivatized drug in water have been employed. Notable technologies include micellar solubilization using surface active ingredients, which will form water soluble micelles containing the drug. Another related technique is complexation of the drug molecule with a host molecule. The host molecule is usually one that has good solubility in water. The host molecule does not form any covalent bonds with the drug molecule but forms a weak complex through non-covalent interactions and the host molecule(s) keep the drug molecule(s) in water solution.

Cyclodextrins are cyclic oligosaccharides which have been recognized as useful pharmaceutical excipients. The common cylcodextrins are called α-, β-, γ- and δ-cyclodextrins depending on the number of glucose molecules in the cyclic oligosaccharide structure. These cyclodextrins are (α1, 4)-linked oligosaccharides of α-D-glucopyranose containing a relatively hydrophobic central cavity and hydrophilic outer surface. These molecules are not exactly perfect cylinders due to restriction of completely free rotation about their linking bonds of the units of the sugar molecule. They assume the shape of a torus or a truncated cone. The secondary hydroxyl groups line the wider edge of the rim while the primary hydroxyl groups line the narrow side of the torus. The solubilities of these molecules in water and the diameter of the central cavity have been known and published (Loftsson, T.; Brewster, M. E.; J Pharmaceutical Sciences, (1996), 85, 1017 & Rajewski, R. A.; Stella, V. J.; J Pharmaceutical Sciences, (1996), 85, 1142). The structure of β-cyclodextrin containing seven glucose units is shown as an example

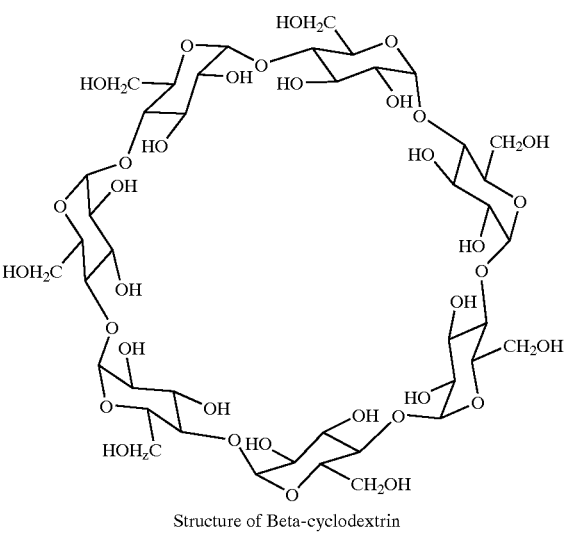

Structure of Beta-cyclodextrin

The α-cyclodextrin has six anhydroglucose molecules in the ring; the γ- and δ-cyclodextrins have eight and nine respectively. The α-, β-, γ- and δ-cyclodextrins have their water solubilties at 25° C. (g/100 ml) 14.5, 1.85, 23.2 & 8.19 respectively. The α-, β-, γ- and δ-cyclodextrins are sometimes called natural cyclodextrins and their solubilities in water are at the lower end of the desirable range. Nevertheless they proved very good solubilizing agents for some of the water insoluble molecules. To increase the aqueous solubilities of these natural cyclodextrins, molecular modifications of these α-, β-, γ- and δ-cyclodextrins have been carried out in the literature.

These modified cyclodextrins have much higher solubilities than their natural counterparts and they can be classified as Methylated derivatives of β-cyclodextrin, 2-hydroxypropylated β- and γ-cyclodextrins, sulfobutylated-β-cyclodextrins, branched cyclodextrins, acylated β- and γ-cyclodextrins.

The cyclodextrins can be methylated by Kuhn-Trischmann methylation, Wacker"s industrial method with methyl chloride under pressure and Hakamori methylation using methylhalogenide and sodium hydride (see, Szente, L.; Szejtli, J.; Advanced Drug Delivery Reviews, (1996), 36, 17). The first two technologies have been used to produce randomly methylated cyclodextrin mixture. On the other hand Hakamori methylation is reported to produce a fully methylated heptakis 2,3,6-tri-O-methylated cyclodextrins. The introduction of methyl substituents in the place of the hydrogens of the hydroxy group of parent β-cyclodextrin dramatically improves the solubility of this randomly methylated cyclodextrin, referred in this invention as RAMEBCD versus the parent β-cyclodextrin.

There are totally 21 hydroxyl groups (14 secondary hydroxyl groups and seven primary hydroxyl groups) in β-cyclodextrin. The aqueous solubility of RAMEBCD increases as the number of methyl groups reaches around 13–14 and decreases as methylation approaches 21 methoxy groups per molecule of β-cyclodextrin. An example of a commercially available RAMEBCD product can be cited the one produced by Wacker Chemie and marketed under the name CAVASOL® W7 M Pharma (CAS no 128446-36-6). Aqueous solubilities of such RAMEBCDs are typically ~220 g/100 ml of water. Such RAMEBCDs have an average degree of methylation ~1.7 to 1.9 per anhydroglucose unit. Such RAMEBCDs are available commercially and have very good aqueous solubilities as noted. The general structure of such RAMEBCDs are shown as follows

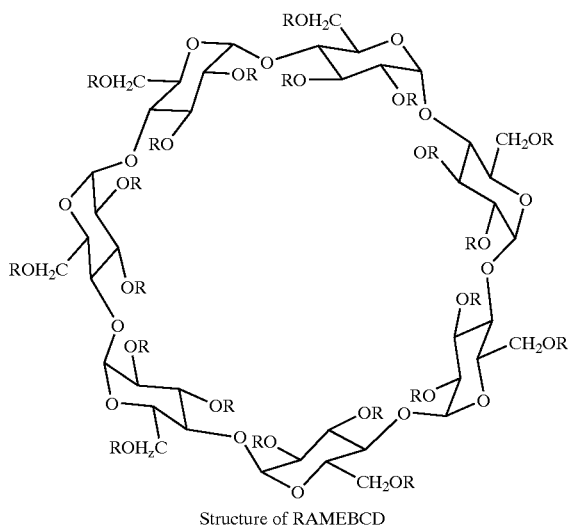

Structure of RAMEBCD

R = CH$_3$ or H

Reacting cyclodextrins with propylene oxide in alkaline solution results in substitution of the hydroxy groups in the cyclodextrins with 2-hydroxypropyl derivatives. A higher substitution of the hydroxyls with propylene oxide also results in the formation of oligomeric hydroxypropylene oxide side chain formation. Such 2-hydroxy-propyl-β-cyclodextrin referred in this invention as HPBCD is represented by the following generic structure. Such materials are available commercially.

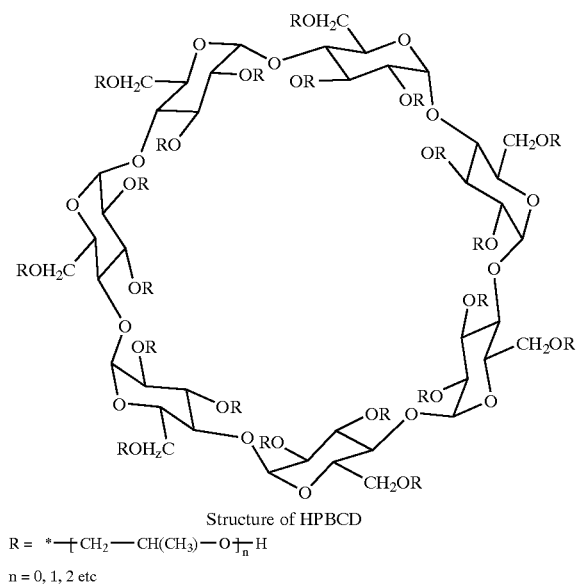

Structure of HPBCD

R = *—[CH$_2$—CH(CH$_3$)—O]$_n$—H n = 0, 1, 2 etc

Similarly to HPBCD, γ-cyclodextrin can be hydroxypropylated to give hydroxypropyl γ-cyclodextrin, referred as HPGCD in this invention. Such materials are available commercially

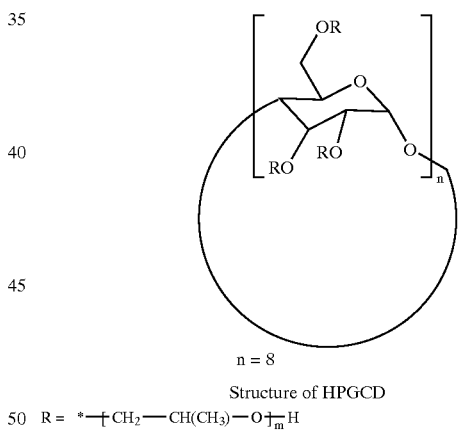

n = 8

Structure of HPGCD

R = *—[CH$_2$—CH(CH$_3$)—O]$_m$—H m = 0, 1, 2 ... etc

A review on the applications of cyclodextrin in the ophthalmic field has appeared (Loftssona, T.; Jarvinen, T.; Advanced Drug Delivery Reviews, (1999), 36, 59). A patent, U.S. Pat. No. 6,346,273 describes the aqueous solubilization of forskolin through the use of polyvinylpyrrolidone and a surfactant, polyethyleneglycol-glyceryl tririicinoleate. The maximum solubility of Forskolin achieved in this patent is 0.2%.

U.S. Pat. No. 4,476,140 describes a composition and method for treatment of Glaucoma by administration of a therapeutically effective amount of a material selected from the group consisting of forskolin, colforsin and polyoxygenated Labdane derivatives. The active agent concentration of 0.1% to 4% is reported herein to be physiologically effective when administered as a topical suspension to the eye.

U.S. Pat. Nos. 5,070,209, 4,978,678, 5,023,344, 4,871,764 describe novel 12-halogenated forskolin derivatives, intermediates and processes for the preparation thereof, and methods for reducing intraocular pressure utilizing compounds or compositions.

EP0268256 describes novel 12-halogenated forskolin derivatives, intermediates and processes for their preparation, and methods for reducing intraocular pressure utilizing the compounds or compositions.

However these prior art references do not describe solubilization of unmodified forskolin to obtain clear aqueous solutions of concentrations of 1% or greater.

SUMMARY OF INVENTION

The invention describes the preparation of aqueous solutions of diterpenes such as Forskolin, that are sparingly soluble or insoluble in water, of concentrations up to approximately 6%. These solutions are prepared using suitably substituted cyclodextrin as a solubilizing agent. In the absence of cyclodextrin, Forskolin is almost insoluble in water yielding solutions of only about 0.001% concentration. Aqueous solutions of forskolin and/or its congeners, containing higher amounts of the active ingredient, can be used topically and systemically to provide diverse health benefits.

DETAILED DESCRIPTION

Forskolin has the following structure

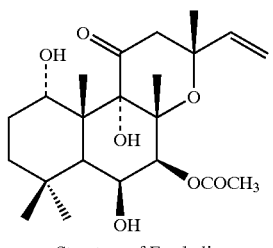

Structure of Forskolin

A closely related isomer is called Isoforskolin and it has the following structure

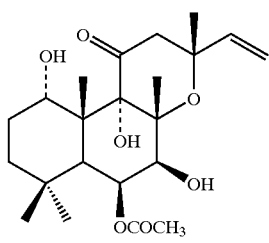

Structure of Isoforskolin

Isoforskolin also has been reported to have many similar pharmacological properties as Forskolin. We have used these six commercially available cyclodextrins, namely, α-, β-, γ-cyclodextrins as well as their derivatized products such as RAMEBCD, HPBCD, HPGCD to solubilize the rather sparingly water soluble Forskolin.

To solubilize Forskolin using cyclodextrins, the chosen cyclodextrin and Forskolin are mixed in water in specific proportions. The aqueous solution is filtered to remove any undissoved particles to obtain a clear aqueous solution of Forskolin in water.

Alternatively, the cyclodextrin and Forskolin in certain proportions are dissolved in a suitable solvent such as ethanol or acetone or ethyl acetate. The solvent is removed to leave behind a white powder. Such powder freely dissolves in water as the examples will illustrate. Further, additives to the aqueous solution of Forskolin can also be added. These additives are usually used for maintaining sterility, pH maintenance, maintenance of osmolarity etc.

A wide variety of choice exists in the selection of such additives. While benzalkonium chloride is used in the illustrative example for preservative, one could equally choose from many others such as Benzethonium chloride, chlorobutanol, methyl paraben, propyl paraben, Thimerosal etc.

An antioxidant such as the disodium salt of EDTA is used to stabilize the preparation; other antioxidants such as sodium bisulfite, sodium metabisulfite, thiourea could be used also among others.

Especially for ophthalmic solutions, viscosity desired for an ophthalmic solution is in the range 25 and 50 cps. Viscosity enhancers such as polyvinyl alcohol, polyvinylpyrrolidone, methyl cellulose, hydroxypropylmethyl cellulose, hydroxyethyl cellulose could be used.

The examples that are described below serve their purpose only as illustrative examples and do not limit in any way the broad scope of this invention.

ILLUSTRATIVE EXAMPLES

Example 1

Determination of the aqueous solubility of Forskolin. Forskolin (300 mg) was dried at 105° C. for 6 hours. Dried Forskolin 200 mg was stirred with 100 ml water for 48 hours for the determination of intrinsic solubility at ambient temperatureResulting solution was filtered through 0.45 μm nylon filter and analyzed for the content of Forskolin by HPLC. Content of Forskolin by HPLC 0.01 mg/ml or 0.001% w/v; In other words Forskolin has a solubility of ~0.001% w/v in water.

Example 2

Forskolin (98.5% assay, 25 mg) was added to 1 ml water containing in the dissolved state 500 mg Hydroxy propyl β cyclodextrin, HPBCD, (~50%) Suspension was agitated at 75 RPM in an isothermal shaker for 60 hours at temperature ~30° C. Resulting solution was filtered through 0.45 μm nylon filter and analyzed for the content of Forskolin by HPLC 1.33 mg/ml or 0.133% w/v.

Example 3

Forskolin (98.5% assay, 50 mg) was added to 1 ml water containing 500 mg Hydroxy propyl γ-cyclodextrin in the dissolved state. (HPGCD) (~50%). Suspension was agitated at 75 RPM in an isothermal shaker for 60 hours at temperature ~30° C. Resulting solution was filtered through 0.45 μm nylon filter and analyzed for the content of Forskolin by HPLC 1.52 mg/ml or 0.152% w/v.

Example 4

Experiments were performed by "changing" the crystallinity of Forskolin by recrystallizing from methylene chloride and from ethyl acetate. Resulting "amorphous" Forskolin was used for complexation with Hydroxyropyl γ-cyclodextrin HPGCD. Forskolin (29.3 mg) recrystallized with methylene dichloride (Forskolin assay 99.0%) was added to 3 ml water containing 1.5 gram Hydroxy propyl γ-cyclodextrin, HPGCD (~50%). Suspension was agitated at 75 RPM in an isothermal shaker for 160 hour at temperature 30° C. Resulting solution was filtered through 0.45 μm nylon filter and analyzed for the content of Forskolin by HPLC 1.74 mg/ml or 0.174% w/v.

Example 5

Forskolin (30.3 mg) recrystallized with ethyl acetate (Forskolin assay 98.8%) was added to 3 ml water containing 1.5 gram Hydroxy propyl γ-cyclodextrin, HPGCD (~50%). Suspension was agitated at 75 RPM in an isothermal shaker for 160 hour at temperature 30° C. Resulting solution was filtered through 0.45 μm nylon filter and analyzed for the content of Forskolin by HPLC 3.38 mg/ml or 0.338% w/v.

Example 6

Forskolin (98.5% assay, 330 mg) was added to 10 ml water containing 4 g of RAMEBCD (~40%). Suspension was agitated at 75 RPM in an isothermal shaker for 40 hours at temperature 30° C. Resulting solution was filtered through 0.45 μm nylon filter and analyzed for the content of Forskolin by HPLC 20.46 mg/ml or 2.046% w/v.

Example 7

Solubility of Forskolin in water was determined at the different concentrations of RAMEBCD ranging from 5 to 66%. The relationship is nearly linear and indicates that the solubility of Forskolin is increased by increasing the concentration of RAMEBCD.

| S.N. | % Concentration of RAMEBCD | % Forskolin w/v |
| --- | --- | --- |
| 1 | 5% RAMEBCD | 0.09 |
| 2 | 10% RAMEBCD | 0.272 |
| 3 | 15% RAMEBCD | 0.767 |
| 4 | 20% RAMEBCD | 1.15 |
| 5 | 40% RAMEBCD | 2.746 |
| 6 | 53.28% RAMEBCD | 4.165 |
| 7 | 66.6% RAMEBCD | 5.029 |

Example 8

A typical aqueous formulation of Forskolin with a cyclodextrin is prepared as follows, RAMEBCD, being used as the example of cyclodextrin RAMEBCD (100 g) is taken in a one liter flask with mechanical or magnetic stirring facility. Forskolin (5.5 g) was charged into the flask. Water (400 ml) is charged to the flask and the contents were agitated at room temperature. A clear solution is obtained. If any undissolved Forskolin particles are seen, they are resuspended and stirred. Benzalkonium chloride (50 mg) and Disodium EDTA (500 mg) are added and dissolved in the flask. The pH of the contents could be adjusted to the desired range with the help of 0.1N sodium hydroxide. (usually pH range 3.5 to 7.5). Calculated amount of sodium chloride solution is added to maintain the osmolarity of the solution equivalent to that of 0.9% sodium chloride. The total volume of the solution is made up to 500 ml after sterile filtration. A solution thus prepared has approximately 1% of Forskolin in the dissolved state. Other cyclodextrins also could be used and depending on the cyclodextrin used, the dissolved content of Forskolin in water differed.

Example 9

Forskolin (50 mg) was dissolved in 5 ml acetone, and 1 gram of RAMEBCD was dissolved in 5 ml acetone separately. Both the solutions were mixed together and solvent acetone was evaporated under reduced pressure. Residue was dried and dissolved in 5 ml water. This residue dissolved very easily within 1 hour of stirring forming a clear colorless solution.

Example 10

Isoforskolin also could be used in place of Forskolin. In one preparation, Isoforskolin (50 mg) was suspended in water containing a suitable amount of a cyclodextrin, for example, R AMEBCD (20 g) in about 100 ml water. After agitation at room temperature, the solution was filtered and the resulting solution was analyzed by HPLC which showed the presence of Isoforkolin approximately 0.5%; The amount of dissolved Isoforskolin could be altered by changing the amount of RAMEBCD.

Example 11

An illustrative example of the biological activity of the preparation is presented. The anti-glaucoma activity of the forskolin composition was studied in albino rabbits. A 1% solution of Forskolin in water as described in example 8 was used for the experiments Study design: Animal model: Albino rabbit Number of groups: 4 Number of animals in each group: 6 in treatment group and 2 in control group Materials and methods: Six albino rabbits of New Zealand strain, of both sexes, weighing 1.0–1.5 lb were chosen. The rabbits were housed in clean and well-ventilated open space. Each rabbit was fed with standard diet daily and water was administered ad libitum throughout the study.

Ocular hypertension was induced by the method reported by Bonomi et al (Invest Ophthalmol. 1976 September; 15(9):781–4.) The rabbits were given 0.3 ml subconjunctival injection of Betnesol containing betamethasone sodium 4 mg/ml, every day to each eye for a period of three weeks (the Intraocular pressure (IOP) at third week was maximum as per literature). Local anesthetic propracaine eye drops were used prior to subconjunctival injections.

In each rabbit the left eye was kept as control for glaucoma and the right eye was treated for glaucoma using Forskolin, Timolol, and the placebo.

For each treatment, the IOP readings were measured at intervals of 30 minutes up to 210 minutes using the non-contact tonometer (NCT).

Results

| Time (mins) | IOP Readings* (mmHg) | | |
| --- | --- | --- | --- |
| | Placebo | Timolol Right eye (treated) | Forskolin |
| 0 | 14 | 13 | 14 |
| 30 | 13 | 8 | 7 |
| 60 | 12 | 7 | 6.5 |
| 90 | 11.5 | 5 | 4.5 |
| 120 | 11 | 4 | 5 |
| 150 | 10.5 | 3.5 | 6 |
| 180 | 10 | 4.5 | 7 |
| 210 | 9 | 6 | 7.5 |

*Average of 6 determinations
IOP of left eye (control) ranged between 12–13 mmHg.
IOP of control group animals ranged between 4–4.5 mmHG.

Statistical Analysis: The IOP readings of the placebo, Forskolin and Timolol were subjected to ANOVA (one way).

The p value was 0.0022 which is very significant, indicating that the variation in column means is not by chance.

The IOP readings of the placebo and forskolin were subjected to "t" test to determine whether the medians of Forskolin and the placebo differ significantly. The p value was found to be 0.0177 which is considered significant. Similarly, the IOP readings of the placebo and Timolol had a "p" value of 0.0087, which is again significant.

The IOP readings of Forskolin and Timolol were also subjected to "t" test. The p value was found to be 0.3999, which is not considered significant., implying that the activity of forskolin preparation is not significantly different from Timolol.

Conclusion: The Forskolin composition has antiglaucoma activity comparable to Timolol.

What is claimed is:

1. A method of solubilizing at least one natural or synthetic forskolin, isoforskolin, or 7-deacetylforskolin in water, the method comprising:
   1) suspending forskolin, isoforskolin or 7-deacetylforskolin in water containing a complexing/solubilizing cyclodextrin agent;
   2) agitating at room temperature; and
   3) filtering to obtain a clear aqueous solution containing 0.09% to 6% of forskolin, isoforskolin, or 7-deacetylforskolin.

2. The method as claimed in claim 1, wherein the at least one natural forskolin, isoforskolin, or 7-deacetylforskolin is obtained from Coleus forskohlii.

3. The method as claimed in claim 1, wherein the complexing/solubilizing cyclodextrin agent is selected from the group consisting of α-, β-, γ-cyclodextrins or their derivatized products, randomly methylated β-cyclodextrin (RAMEBCD), 2-hydroxy-propyl-β-cyclodextrin (HPBCD), and hydroxypropyl γ-cyclodextrin (HPGCD).

4. The method as claimed in claim 3, wherein prior to step 1), the cyclodextrin agent and forskolin, isoforskolin, or 7-deacetylforskolin are dissolved in a solvent under agitation, wherein the solvent is selected from the group consisting of ethanol, acetone, ethyl acetate, and methylene chloride, followed by removal of the solvent and suspending and dissolving the residue in water.

5. The method of claim 1, wherein the clear aqueous solution is suitable for ophthalmic, topical and systemic uses.

6. A method of solubilizing at least one natural or synthetic forskolin, isoforskolin, or 7-deacetylforskolin in water, the method comprising:
   1) dissolving forskolin, isoforskolin or 7-deacetylforskolin in an organic solvent selected from ethanol, acetone, ethyl acetate and methylene chloride;
   2) recrystallizing forskolin, isoforskolin or 7-deacetylyforskolin from the organic solvent;
   3) complexing the forskolin, isoforskolin or 7-deacetylforskolin in water containing a complexing/solubilizing cyclodextrin agent selected from the group consisting of α-, β-, γ-cyclodextrins or their derivatized products, randomly methylated β-cyclodextrin (RAMEBCD), 2-hydroxy-propyl-β-cyclodextrin (HPBCD), and hydroxypropyl γ-cyclodextrin (HPGCD);
   4) agitating at room temperature for 4 to 160 hours; and
   5) filtering to obtain a clear aqueous solution containing 0.09% to 6% of forskolin, isoforskolin, or 7-deacetylforskolin.

7. A method of solubilizing at least one natural or synthetic forskolin, isoforskolin, or 7-deacetylforskolin in water, the method comprising: 1) suspending forskolin, isoforskolin or 7-deacetylforskolin in water containing randomly methylated β-cyclodextrin (RAMEBCD);
   2) agitating at room temperature; and
   3) filtering to obtain a clear aqueous solution containing 0.09% to 6% of forskolin, isoforskolin, or 7-deacetylforskolin.

* * * * *